US00PP10117P

United States Patent [19]

Molyneaux et al.

[11] Patent Number: Plant 10,117

[45] Date of Patent: Nov. 11, 1997

[54] HARDENBERGIA PLANT NAMED 'FREE 'N' EASY'

[75] Inventors: William Mitchell Molyneaux; Susan Glen Forrester, both of Dixons Creek, Australia

[73] Assignee: Austraflora Pty. Ltd., Montrose, Australia

[21] Appl. No.: 648,926

[22] Filed: May 16, 1996

[51] Int. Cl.[6] ..... A01H 5/00

[52] U.S. Cl. ..... Plt./54.1

[58] Field of Search ..... Plt./54.1

*Primary Examiner*—James R. Feyrer

*Attorney, Agent, or Firm*—C. A. Whealy

[57] ABSTRACT

A distinct cultivar of Hardenbergia plant named Free 'N' Easy, characterized by its spreading, sprawling growth habit; vigorous and rapid growth rate; freely branching; dense growth; white flowers with a reddish purple blotch on the back of the standard petal; and early flowering.

2 Drawing Sheets

The present invention relates to a new and distinct cultivar of Hardenbergia plant, botanically known as *Hardenbergia violacea* and referred to by the cultivar name Free 'N' Easy.

The new cultivar is a spontaneous mutation of the commercial cultivar Happy Wanderer (not patented). The new cultivar was discovered and selected by the inventors in Dixons Creek, Victoria, Australia, as a single plant among a population of plants of the cultivar Happy Wanderer. This single plant consistently formed inflorescences having white flowers with a reddish purple blotch on the back of the standard, or upper, petal in contrast to the violet colored flowers of plants of the cultivar Happy Wanderer. In side-by-side comparisons in Montrose, Victoria, Australia, plants of the new Hardenbergia consistently flower 4 to 6 weeks earlier than plants of the cultivar Happy Wanderer. A detailed comparison of plants of the new Hardenbergia and the cultivar Happy Wanderer appears in Chart A at the end of the specification.

Asexual reproduction of the new cultivar by terminal cuttings taken at Montrose, Victoria, Australia, has shown that the unique features of this new Hardenbergia are stable and reproduced true to type in successive generations. The following traits have been repeatedly observed and are determined to be the unique characteristics of Free 'N' Easy. These characteristics in combination distinguish Free 'N' Easy as a new and distinct cultivar:

1. Spreading, sprawling growth habit, can be grown as a climbing or ground cover plant.
2. Vigorous and rapid growth rate.
3. Freely branching.
4. Dense growth.
5. White flowers with a reddish purple blotch on the back of the standard petal, yellow green eye on front of standard petal.
6. Early flowering.

The cultivar Free 'N' Easy has not been observed under all possible environmental conditions. The phenotype may vary somewhat with variations in environment such as temperature and light intensity, without, however, any variance in genotype.

The accompanying colored photographs illustrate the overall appearance of the new cultivar, showing the colors as true as it is reasonably possible to obtain in colored reproductions of this type. The first photograph comprises a side perspective view of a typical flowering plant of Free 'N' Easy. The second photograph comprises a close-up view of leaves and flowers of the cultivar Free 'N' Easy.

In the following description, color references are made to The Royal Horticultural Society Colour Chart except where general terms of ordinary dictionary significance are used. The following observations and measurements describe plants grown in Montrose, Victoria, Australia under outdoor conditions with temperatures ranging from −2 to 40C.

Botanical classification: *Hardenbergia violacea* cultivar Free 'N' Easy.

Commercial use: Outdoor climbing or ground cover plant.

Parentage: Spontaneous mutation of the cultivar Happy Wanderer (not patented).

Propagation:

*Type.*—By terminal cuttings and also by tissue culture.

*Roots.*—Thick and freely branching.

Plant description:

*Form.*—Spreading and sprawling, can be trained vertically or used as a prostrate ground cover.

*Growth habit.*—Vigorous, rapid growth rate. Freely branching with short internodes, dense growth.

*Plant size.*—As a climbing plant, plants are usually 2 to 3 meters tall and 3 to 4 meters wide.

*Foliage description.*—Leaves arranged alternately, single, generally symmetrical, abundant, and flat in aspect. Leaf size: Length: About 8 cm. Width: About 4 cm. Shape: Broadly lanceolate with acute tip and blunt leaf base. Texture: Dull, glabrous and leathery. Margin: Entire. Venation pattern: Pinnate. Color: Young foliage, upper side: 152B. Young foliage, under side: 152B. Mature foliage, upper side: 147A. Mature foliage, under side: 147A.

Flower description:

*Flower type and habit.*—Flowers are borne singly on long racemes that are either single or branched and formed at leaf axils. Freely flowering.

*Natural flowering season.*—Commences flowering in mid-May and continues to late September in the Southern Hemisphere.

*Raceme length.*—About 40 cm.

*Quantity of flowers.*—Up to 92 per raceme or an average of about 67 per raceme.

*Flower diameter.*—About 1 cm.

*Flower depth (height).*—About 7 mm.

*Flower longevity on plant.*—About 2 weeks.

*Fragrance.*—Slight.

*Persistent.*—No.

*Flower buds.*—Size: About 5 mm. Color: White, 155D, with reddish purple, 64B, blotch on the back of the standard petal.

*Petals.*—Size: Length: About 1 cm. Width: About 7 mm. Shape: Rounded. Texture: Smooth. Margin:

Entire. Color: White, 155D, flowers with a reddish purple, 64B, blotch on the back of the standard petal. Yellow green, 144C, eye on front of standard petal.

*Calyx.*—Size: About 2 mm. Shape: Funnel, dentate. Texture: Glabrous. Color: 187A.

*Peduncles.*—Strong but flexible, drooping. Length: About 1.6 cm.

Disease resistance: Occasionally susceptible to mildew with high humidity.

Seed production: Seed production has not been observed.

CHART A

| CHARACTERISTIC | FREE 'N' EASY | HAPPY WANDERER |
|---|---|---|
| LEAF COLOR, YOUNG LEAVES | Yellow green, 152B | Green, 143A |
| FLOWER COLOR | White, 155D, flowers with a reddish purple, 64B, blotch on the back of the standard petal Yellow green, 144C, eye on front of standard petal | Violet, 84A and 87A Yellow green, 144C, eye on front of standard petal |
| QUANTITY OF FLOWERS PER RACEME | An average of 67 per raceme | An average of 58 per raceme |
| CALYX COLOR | Reddish brown, 187A | Light green, 144D |
| COMMENCEMENT OF FLOWERING | Mid-May | Late June |

It is claimed:

1. A new and distinct cultivar of Hardenbergia plant named Free 'N' Easy, as illustrated and described.

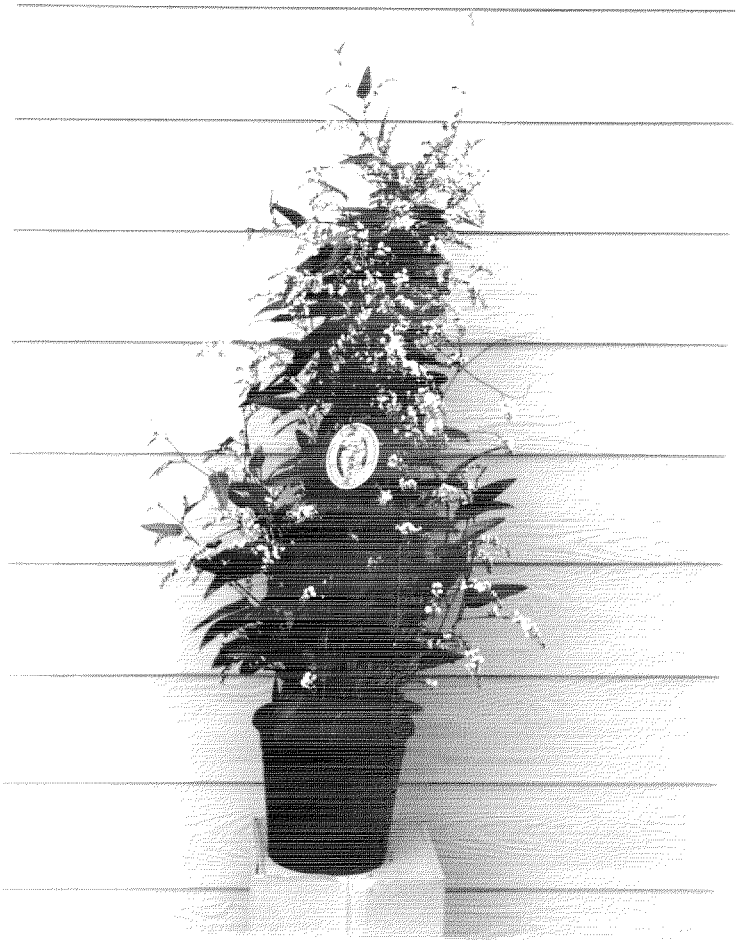

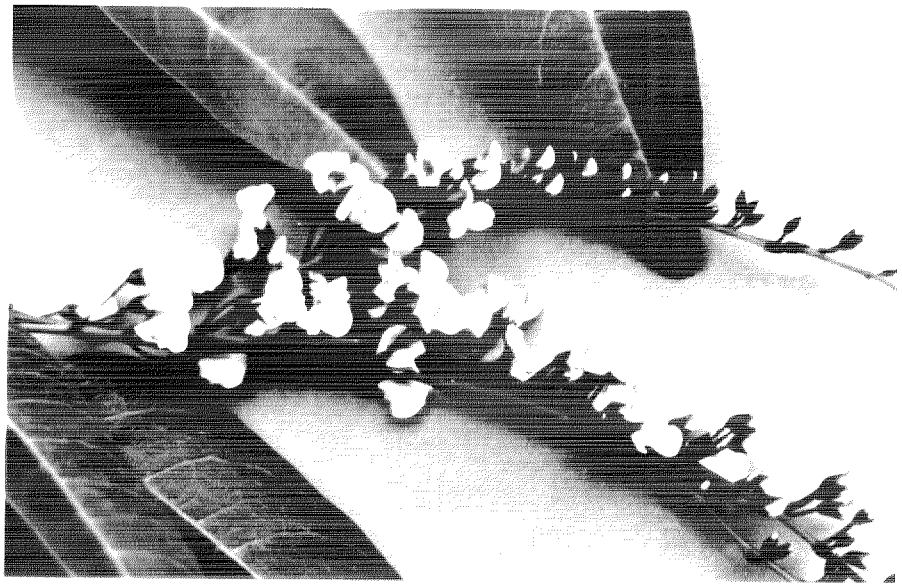

* * * * *